United States Patent [19]
Jacquot et al.

[11] Patent Number: 5,973,210
[45] Date of Patent: *Oct. 26, 1999

[54] INTERMETALLIC RUTHENIUM TIN-CATALYST FOR USE IN ALDEHYDE SYNTHESIS

[75] Inventors: Roland Jacquot, Sainte-Foy-les-Lyon; Jean-Marc LeClercq, Domont; Claude Mercier, Lyon; Jean-Michel Popa, Drancy, all of France

[73] Assignee: Rhone-Poulenc Chimie, Courbevoie, France

[*] Notice: This patent issued on a continued prosecution application filed under 37 CFR 1.53(d), and is subject to the twenty year patent term provisions of 35 U.S.C. 154(a)(2).

[21] Appl. No.: 08/716,399
[22] PCT Filed: Jan. 22, 1996
[86] PCT No.: PCT/FR96/00101
 § 371 Date: Jul. 31, 1997
 § 102(e) Date: Jul. 31, 1997
[87] PCT Pub. No.: WO96/22832
 PCT Pub. Date: Aug. 1, 1996

[30] Foreign Application Priority Data

Jan. 23, 1995 [FR] France .................................. 95 00699

[51] Int. Cl.⁶ .................................................. C07C 45/00
[52] U.S. Cl. .......................... 568/484; 502/326; 502/261; 502/349; 502/352

[58] Field of Search ...................................... 502/242, 261, 502/326, 349, 352; 568/484; 556/136

[56] References Cited

U.S. PATENT DOCUMENTS 5,393,919  2/1995  Shinoda ................................... 560/239
5,476,827  12/1995 Ferrero ..................................... 502/227

OTHER PUBLICATIONS

CA;86:198283 abst of "Bonding in iron—tin and ruthenium–tin mixtures", Heinrich, J Less Common Met, 52(1), pp. 87–91. 1977.

*Primary Examiner*—Peter O'Sullivan
*Assistant Examiner*—Jean F Vollano
*Attorney, Agent, or Firm*—Andrew M. Solomon

[57] ABSTRACT

The present invention relates to a composition which can be used as reduction catalyst.

This composition is characterized in that it comprises a support whose constituent material comprises at least one oxide chosen from oxides which are inert or capable of being made inert relative to the reaction mixture and a phase at least partially covering the said support, of which at least part comprises an intermetallic ruthenium-tin compound of composition $Ru_3Sn_7$. The invention also describes the use of the reduction catalyst and its application to organic synthesis.

12 Claims, No Drawings

INTERMETALLIC RUTHENIUM TIN-CATALYST FOR USE IN ALDEHYDE SYNTHESIS

This application is a continued Prosecute Application of application Ser. No. 08/716,399, filed: Jul. 31, 1997, which is a 371 of international application number PCT/FR96/00101, filed Jan. 22, 1996.

The present invention relates to a process for preparing aldehydes and derivatives thereof by vapour-phase reduction in the presence of hydrogen, acids, esters or carboxylic anhydrides.

It relates more particularly to a process for the synthesis of aldehydes by vapour-phase reduction of acids, esters or derivatives thereof in the presence of a bimetallic catalyst of the ruthenium/tin type. It also relates to a catalyst and to its use for the selective reduction of carboxylic derivatives to aldehydes.

The present process relates more particularly, as substrate, to carboxylic compounds which carry halogen, and especially fluorine, and are capable of undergoing hydrogenolysis in the course of reduction.

It is known in the prior art to prepare saturated aliphatic or aromatic aldehydes by reduction of the corresponding esters or acids using a catalyst chosen from the oxides of cerium, zirconium, uranium, praseodymium and yttrium at a temperature of between 350 and 450° C. (U.S. Pat. No. 4,328,373).

Owing to the temperature conditions required for their implementation, these processes do not permit preparation of aldehydes from thermally unstable acids.

The patent application published under the U.S. Pat. No. 2,682,949 described a technique using alloys of ruthenium and tin which permits a significant improvement.

Catalysts of the Ru/Sn/B type had already been described in the literature [J. Cat., 121, 165–173 (1990)], as had their use for the liquid-phase reduction of unsaturated fatty acids to unsaturated fatty alcohols [J. Cat., 121, 174–182 (1990)].

Certain problems remained unresolved. For a certain number of substrates, giving rise to secondary reactions, the choice of the support and of the manner in which the surface catalytic layer was formed was found to be critical. The problem is particularly acute in the case of the reduction of certain halogenated derivatives, whose lysis by hydrogen leads to particularly aggressive acids such as, for example, hydrofluoric acid.

These acids are capable of destroying certain supports and interfere with the desired reaction. A further risk lies in a catalysis of the reduction of the aldehyde to alcohol.

For this reason, one of the aims of the present invention is to provide a composition which can be used as catalyst and permits improved resistance to products of any secondary reaction(s).

Another aim of the present invention is to provide a composition of the above type which avoids the secondary reactions or reduces their relative importance.

These and other aims which will become evident below are achieved by a composition which can be used as reduction catalyst and which comprises a support whose constituent material comprises at least one oxide chosen from oxides which are inert or capable of being made inert relative to the reaction mixture and a metallic phase at least partially covering the said support, of which at least part comprises an intermetallic ruthenium-tin compound at least some of which is in the form of the defined compound $Ru_3Sn_7$.

The phase containing the ruthenium and the tin advantageously has an Sn/Ru atomic ratio which is at least equal to 2/3, advantageously to 3/2, preferably to 7/3. Moreover, it is preferable for the Sn/Ru atomic ratio to be at most equal to 3, advantageously to 5/2.

The said phase covering at least part of the said support advantageously contains at least 50%, more advantageously 80%, preferably at least 90%, of the said intermetallic phase.

Finally, it is desirable for at least 90%, advantageously at least 95%, preferably 98%, of the ruthenium present on the support to be in the form of the said phase covering the said support.

The invention is more particularly suitable for the preparation of aldehydes of general formula:

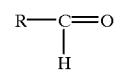

(I)

in which R represents a hydrogen atom or an optionally substituted hydrocarbon radical containing 1 to 40 carbon atoms which can be a linear or branched, saturated or unsaturated acyclic aliphatic radical or a monocyclic or polycyclic, saturated, unsaturated or aromatic carbocyclic or heterocyclic radical, by reduction of esters, anhydrides or acids of formula:

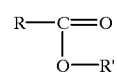

(II)

in which:
R is defined as above,
R' represents:
   a group R as defined above,
   a group

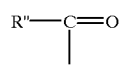

in which R" has the meaning given for R,
   it being possible for the two groups R and R" to be linked to one another to form a saturated or unsaturated ring having 5 to 7 atoms and including the anhydride functional group, and
   it being possible for the two groups R and R" together to form, by way of two vicinal atoms, a bridge of an ortho-condensed bicyclic system.

The carboxylic acids or derivatives preferably employed correspond to the formula (II) in which R represents an optionally substituted hydrocarbon radical containing 1 to 20 carbon atoms.

The invention is quite suitable for the preparation of aldehydes from halogenated aliphatic carboxylic acids, such as fluoral.

The invention is highly suited to the synthesis of aldehydes from aromatic carboxylic acids and halobenzoic acids, preferably fluorobenzoic acids.

In the following description of the present invention the term aromatic compound is understood as denoting the traditional idea of aromaticity as defined in the literature, in particular by Jerry MARCH—Advanced Organic Chemistry, 3rd edition, John Wiley and Sons, 1985, p. 37 et seq.

The term benzoic acid refers to any benzenic compound carrying at least one COOH functional group.

As indicated above, it is also possible to employ the carboxylic acid as defined above in the form of its ester. In this case, in the formula (II), R' preferably represents an optionally substituted aliphatic radical containing 1 to 10 carbon atoms. More preferably, R' represents a linear or branched alkyl radical having 1 to 6 carbon atoms.

Examples of preferred radicals R' which may be mentioned are the radicals methyl, ethyl or hexyl.

The invention is particularly well suited to the synthesis of aldehydes whose formulae include one or more halogens, especially when at least some of these halogens are fluorines.

The invention is aimed particularly at aldehydes obtained from perhalocarboxylic acids or acids which are equivalent to these in terms of their reactivity. Thus equivalents of perhalocarboxylic acids are acids whose vicinal carbon, or rather the two carbons vicinal to the carboxyl functional group, are perhalogenated.

Thus the invention is particularly well suited to the synthesis of aldehydes where the vicinal carbon, or rather the two vicinal carbons, are perfluorinated.

In accordance with the present invention it is possible to employ a carboxylic acid in the form of its anhydrides and esters.

Examples of carboxylic anhydrides which may be mentioned more particularly are the homoanhydrides, which may be internal (cyclic anhydrides) or otherwise, and heteroanhydrides (or mixed anhydrides).

The preferred compounds are bicyclic and are formed from a benzene ring.

The process of the invention is carried out in the gaseous phase. The reaction is advantageously conducted at a temperature of between 100° C. and 500° C., more preferably between 200 and 400° C. It is understood that the temperature is adapted by the person skilled in the art in dependence on the starting acid and on the desired reaction rate.

As has been mentioned above, it is highly desirable for the phase containing the ruthenium and the tin to have an Sn/Ru atomic ratio which is at least equal to $2/3$, advantageously equal to $3/2$, preferably equal to $7/3$. Moreover, it is preferable for the Sn/Ru atomic ratio to be at most equal to 3, advantageously to $5/2$.

In the course of the study which led to the present invention, in order to obtain such values it was shown how important it was to carry out forced reduction at relatively high temperature so as to attain the above proportions of tin. Indeed, in the above proportions the tin contents take account only of metallic tin.

The documents of the prior art describe only mild reduction techniques which appear to be entirely inadequate for reducing tin in order to approach the optimum zone corresponding to the intermetallic compound $Ru_3Sn_7$.

In effect it has been shown that, in order to obtain optimum effects, the reduction described in the prior documents was inadequate to the extent that the intermetallic $Ru_3Sn_7$ compound, if it existed, was in proportions which were too low for it to play its part as a selective catalyst.

It is possible to obtain an intermetallic phase according to the present invention by impregnating the support with salts or oxides and subjecting it to reduction by a stream (for example under at least $2 \times 10^5$ Pa) of hydrogen (or of a gas which is a source of hydrogen under the conditions of the process, such as propylene and, for instance, ethylene) at a temperature of at least 400° C., preferably at least 450° C. The impregnating substance includes a proportion of tin which is at least equal to that of $Ru_3Sn_7$ and is preferably significantly greater.

The lower the temperatures, the longer the treatment must last. At a temperature of 400° C. one day is a minimum, whereas this minimum is only about 5 hours at 450° C. In a first stage, it appears that the ruthenium catalyses the reduction of the tin and that, under these conditions, the excess tin is at least partly eliminated and that the intermetallic phase on the support comes close to the $Ru_3Su_7$ composition. The longer the duration of this stage, the closer one comes to the optimum composition of the catalyst, with the proviso that an excess of tin is available.

A practical method of implementing the present invention consists in introducing a desired quantity of catalyst into a reactor. The temperature of the reactor is then raised under a stream of hydrogen to a predetermined value, enabling activation of the catalyst, and then brought to the reaction temperature. The acid is subsequently injected at the desired rate and the aldehyde formed is recovered.

The acid is preferably injected directly in gaseous form after having been vaporized by heating.

However, it can also be injected in solution in a solvent which is inert for the reaction. As inert solvents particular mention may be made of aliphatic hydrocarbons (for example hexane), alicyclic hydrocarbons (for example cyclohexane), aromatic hydrocarbons (for example toluene) or ethers (for example dimethoxyethane). Under the effect of the temperature, the acid thus injected is vaporized. The hydrogen can be injected at atmospheric pressure or under a slight superatmospheric pressure which is compatible with the vapour phase (a partial pressure of a few bars, for example from 0.5 to 10 bar, the bar here being taken to represent $10^5$ Pa). The hydrogen can also be diluted in a gas which is inert under the operating conditions, such as nitrogen or helium.

Advantageously for 1 ml of catalyst, the hydrogen is injected at a rate of between 0.1 and 10 liters per hour and the acid at a liquid flow rate of not more than 10 ml/h and preferably between 0.5 and 5 ml/h.

At the end of the reaction, the aldehyde is recovered by any suitable means, such as distillation or crystallization. In certain cases, especially in the case of fluoral, the aldehyde can be obtained in a hydrated form.

The content of any extraneous element(s) such as boron is generally less than 1% and preferably less than 0.1% in molar terms.

Generally, the two metals in the form of salts are dissolved in water, optionally in the presence of the support, and impregnation is allowed to take place over a period of approximately 15 hours. The support is then dried (for example under vacuum) before being used.

One of the processes for its preparation consists, for example, in introducing a support into a solution which is prepared by dissolving at least one appropriate compound of the chosen elements; the deposition of the active elements on the support is carried out by distilling the solvent, preferably water, which can be eliminated by evaporation under a reduced pressure which is chosen, preferably, between 5 and 20 mm of mercury. The catalyst mass thus obtained is subjected to reduction by means of a stream of hydrogen.

According to another, conventional mode of preparation, the deposition of the compound or compounds providing the metallic elements on the support is carried out by means of compounds which have been precipitated beforehand in a manner known per se, and by subjecting the catalyst mass thus obtained to reduction by means of hydrogen.

The deposition on the support of two or more metallic elements may of course be carried out in succession, but preferably simultaneously.

The deposition of the precursors of the intermetallic phase can be carried out by repeating one of the abovementioned processes. This repetition can be carried out either for repeat impregnations or for repeat cycles of impregnation-reduction.

The nature of the compounds providing the metallic elements which are used for the preparation of the catalysts of the invention is not critical provided that there is no risk of modification of the tin/ruthenium ratio before the great majority (at least ¾, advantageously 9/10, preferably 95%) of the ruthenium has entered into a metallic phase with the tin.

It is possible to employ the metals themselves, such as ruthenium and tin.

As examples of compounds which can be employed for the preparation of the catalysts of the invention mention may be made, by way of ruthenium compounds, of ruthenium (III) chloride, ruthenium(IV) chloride, ruthenium pentafluoride, ruthenium(II) oxide, ruthenium(IV) oxide, ammonium ruthenium oxychloride $Ru_2(OH)_2Cl_4.7NH_3.5H_2O$, and ruthenium acetate, and, by way of tin compounds, of tin oxides, chlorides, nitrates, carboxylates and alcoholates or organometallic compounds in which the tin is linked to a hydrogen atom and/or to alkyl radicals having preferably 1 to 4 carbon atoms. The preferred salts are as follows: ruthenium compounds such as ruthenium(III) chloride, and tin compounds such as tin(II) chloride, tin(IV) chloride, tin(II) acetate, tin(II) octoate and tin ethylhexanoate.

It would not be departing from the scope of the present invention to manufacture, in accordance with the process of the invention, the aldehydes in the form of their derivatives, such as their acetals, their hemiacetals or their bisulphite combinations, by reacting the aldehyde and the reactant [alcohol in the case of the (hemi)acetals] which is introduced either conjointly with the acid, when the reactant is volatile, or at the end of reaction. As examples of alcohols which can conventionally be used mention may be made of methanol or ethanol.

One of the most important aspects of the invention lies in the choice of support.

The support must be chosen in order to maximize the resistance to the industrial conditions, and in particular the resistance to mechanical or quasi mechanical abrasion, especially the resistance to attrition.

The support must be chosen so as to avoid substantial head losses while permitting good contact between the gases and the catalyst.

The support must be chosen from oxides which are inert (i.e. have a good chemical resistance to) or are capable of being made inert relative to the reaction mixture. The problem is particularly acute in the case where the chosen substrate comprises carboxylic acids having halogen atoms, especially fluorine atoms.

In this case it is preferable for the support to show significant resistance to wet halohydric acids, and especially to wet gaseous hydrofluoric acid (the reduction to aldehyde of an acid produces water).

The said support is advantageously one which is capable of being made inert by the action of the gaseous hydrofluoric acid without losing its external geometry and its mechanical strength.

The various silicas are not resistant to the action of hydrofluoric acid.

It should be noted that supports of the charcoal type should be avoided in particular, since they promote secondary reactions and give rise to intense coking of the substrates.

Metal oxides which can be chosen are those such as the oxides of aluminium or of zirconium. Mixed oxides are also suitable, more especially those containing at least ¼, advantageously ⅓, preferably ⅖ by mass of aluminium expressed as $Al_2O_3$.

The said support advantageously has a silicon content which, expressed as $SiO_2$, is at most equal to ⅔ of the total weight, advantageously at most equal to ¼.

The ceramics obtained by firing, at at least approximately 1000° C., clays containing as principal elements the oxides of aluminium and of silicon have been tested and found to give particularly advantageous results. As silicoaluminous clay giving good results mention may be made of Provins clays, especially those sold by Denain Anzin Minéraux under the trade name chamotte 40/42.

The said support advantageously has a particle size such that its $d_{20}$ is at least equal to 0.1 millimeter, advantageously to 0.5 millimeter, preferably to one millimeter.

A good compromise consists in choosing beads of low porosities of from 1 mm to 1 cm, giving good results.

The specific surface area of the support is advantageously low, less than 10 m² per gram, preferably at most equal to 1 m² per gram.

The mass ratio between the support and the surface phase is between 1% and 30%, advantageously from 1 to 15%, preferably from 2 to 10%.

A further aim of the present invention is to provide a process which makes it possible to prepare the composition according to the present invention.

Another aim of the present invention is to provide a process of the above type which makes it possible to obtain a covering phase which is as close as possible to the intermetallic ruthenium-tin compound of composition $Ru_3Sn_7$.

These aims and others which will become evident from what follows are achieved by means of a process comprising the following steps:

a) coating of the support by means of a solution or a suspension of stanniferous and rutheniferous species, the Sn/Ru atomic ratio being at least equal to 2.3, advantageously to 3, preferably to 4;

b) treatment at a temperature at least equal to 400°, advantageously to 450° C., under a partial pressure of hydrogen which is at least equal to ½×10⁵ Pa, advantageously between 1 and 10 bar, preferably between one and two bar, for a period of at least approximately five hours, preferably at least 10 hours.

It is desirable for the choice of stanniferous and rutheniferous species to be made such that it minimizes volatilization during the reduction stage.

The following, non-limiting examples illustrate the invention:

CATALYST I

Example 1

Preparation of a Batch of 9 Liters of 3.5% Ru/ex-clay bead catalyst with an Sn/Ru ratio of 2.3

Preparation of the tin hydroxide suspension

Tin hydroxide is obtained by neutralizing $SnCl_4.5H_2O$ with aqueous ammonia. 5 kg of $SnCl_4.5H_2O$ are dissolved in 3.1 liters of water.

13.45 liters of 5 M ammonia solution are then prepared by diluting 5 liters of 28% aqueous ammonia.

Immediately before neutralizing the tin salt solution with aqueous ammonia, this solution is diluted with 8.6 liters of water in order to give a tin salt concentration of 1.25 M.

Permanent and continuous precipitation is carried out in a one-liter reactor fitted with a stirrer, a temperature control means, a continuous pH regulator, a level regulator and two feed pumps.

Downstream of this precipitation reactor there is a "reservoir" reactor with a capacity of 10 liters for storage.

The initial charge is 1 liter of purified water.

The tin chloride solution is fed in at a constant flow rate of 2.5 l/h. The feeding of the ammonia solution depends on the pH regime imposed and on the deviation from this regime. The chosen pH of precipitation is 5. The stirrer is set at 700 rpm and the temperature is regulated at 30° C.

Once the conditions relating to level have been attained, the suspension is drawn by suction out of the reactor.

Only after 5 passes is the reactor considered to be in a permanent regime, and only after this time is the gel obtained collected in the reservoir reactor.

Filtration is carried out through a Buchner funnel in order to evacuate the mother liquors. The gel is subsequently repulped in 20 liters of purified water and the mixture is stirred for 6 hours. The suspension is subjected to decantation for 12 hours, and then filtered again in order to separate the gel from the washing liquors.

The tin hydroxide gel thus obtained has a water content which varies depending on the filtration efficiency and is measured by way of a loss on ignition at 1000° C. between 55 and 70%.

Preparation of the active-phase precursor

The water content of the hydroxide gel, measured by the loss on ignition at 1000° C., is 57% in this example.

By mixing the tin hydroxide gel and the hydrated salt of Ru(III) chloride, 4414 g of precursor are prepared containing 1361 g of anhydrous $SnO_2$ and 397 g of Ru (in the form of 957 g of $RuCl_3.xH_2O$ containing 43% Ru).

The following description of the preparation of the precursor is related to 1000 g of tin hydroxide gel containing 57% of water.

2.9 mol of $RuCl_3.xH_2O$ containing 43% of Ru (or 293.1 g of Ru) are added to 1000 g of hydroxide gel containing 57% of water, i.e. 6.66 mol of $SnO_2$.

For rapid mixing of the hydroxide and the salt (approximately 1 hour), 260 g of water are added to the mixture, bringing the hydroxide gel to a water content of 65%; the paste thus obtained is highly fluid.

Therefore, 79 g of Degussa OX-50 silica are added as thickener so as to obtain the appropriate viscosity for coating.

2548 g of active-phase precursor are prepared in this way.

A variant consists in mixing the tin hydroxide gel and the Ru salt by mechanical stirring for a long period (24 h) without additionally adding either water or silica.

Coating of the active-phase precursor on the T375 bead support

The 9 liters of T375 beads (11.25 kg) are placed in a film-coating apparatus whose volume, the angle of the axis of rotation and the speed of rotation are chosen so as to avoid the loss of beads by expulsion from the film-coater and to obtain a vacant central area in the bed of rotating beads.

The active-phase precursor prepared above is then poured gradually into the rotating film-coater.

The coating of the beads by the active-phase precursor is perfectly homogeneous.

The addition of precursor is stopped when the beads are seen to have a shiny, slightly wet appearance.

Degussa OX-50 silica is then poured into the bed of rotating beads.

Rotation is then maintained for approximately 30 minutes in order to complete the coating of the layer of the precursor with silica.

The catalyst thus obtained is oven-dried under a vacuum of 540 mm Hg at 80° C.

The height of the catalyst bed in the boat is limited to 2 cm.

Drying lasts between 5 hours and 16 hours.

After drying, the catalyst is replaced in the film-coater in order to carry out the second coating of precursor.

The desired percentage of Ru is attained after 6 active-phase precursor coating operations.

The series of coating operations of active-phase precursor and silica for the preparation of the catalyst I is set out in the table in annex I.

The catalyst is ready for loading into the catalytic reactor where it will be activated by reduction under hydrogen.

CATALYST II

Example 2

Preparation of a Batch of 9 Liters of 3.1% Ru/ex-clay bead catalyst with an Sn/Ru ratio of 3

The above preparation is reproduced with an Sn/Ru ratio of 3.

The preparation of the tin hydroxide gel follows the same procedure.

In this case the tin hydroxide gel has a water content after filtration, measured by its loss on ignition at 1000° C., of 65%.

The mixture of this hydroxide gel with the Ru salt at an Sn/Ru ratio of 3 gives a paste which is too fluid to be applied as a coating to the beads.

Drying under vacuum at 120° C. of the tin hydroxide makes it possible to reduce the residual water content to 57% (loss on ignition at 1000° C.).

The mixture of this tin hydroxide gel containing 57% of water with the Ru(III) chloride salt in accordance with the above-described procedure (stirring for 24 hours) gives an active-phase precursor with an Sn/Ru ratio of 3 which is suitable for carrying out coating.

A slightly greater fluidity of the precursor relative to the previous preparation, and the use of a smaller quantity of silica for coating and stabilizing the successive layers of precursors ((149 g instead of 414 g), make it necessary to carry out a total of 8 coating operations in order to attain the desired percentage of Ru.

The totality of coating operations for the preparation of the catalyst II is set out in the table in annex II.

The alumina beads were treated in 2 batches, as described above.

Example 3

Example of the Preparation of Fluoral Hydrate $CF_3CH(OH)_2$ by Selective Reduction of Trifluoroacetic Acid $CF_3COH$ (TFA) by Hydrogen Gas in the Presence of a Catalyst whose Active Phase, $Ru_3Sn_7$, is Deposited on Alumina Beads 28 g of catalyst are charged to a stainless-steel reactor (316 l) with a length of 30 cm. Following activation of the catalyst at elevated temperature in a stream of hydrogen, the catalyst bed is fed, under a constant stream of hydrogen, with trifluoroacetic acid at a temperature of between 250 and 400° C., the $H_2$/TFA molar ratio being between 1.5 and 4.

The crude reaction mixture is collected in a cold trap and then, following customary treatment, is analysed by gas chromatography:

selectivity for fluoral hydrate: 73% conversion of the TFA: 75%

Similar tests using support phases of different types of alumina give similar results.

CATALYST I: Preparation of a batch of 9 liters of 3.5% Ru/T375 ex-clay bead catalyst with an Sn/Ru ratio of 2.3

|  | Weight of active phase (g) | % of SnO$_2$ in the active phase | g of SnO$_2$ introduced | % Ru in the active phase | g of Ru introduced | Total Ru introduced (g) | % Ru/beads | % Ru relative to precursor | % Ru relative to recovered mass | g of Degussa 50 SiO$_2$ introduced |
|---|---|---|---|---|---|---|---|---|---|---|
| 1st coating | 639 | 30 | 190 | 8.7 | 56 | 56 | 0.5 |  |  | 141 |
| 2nd coating | 975 | 30 | 290 | 8.7 | 85 | 140 | 1.2 |  |  | 219 |
| 3rd coating | 584 | 30 | 174 | 8.7 | 51 | 191 | 1.7 |  |  | 17 |
| 4th coating | 477 | 30 | 145 | 8.4 | 40 | 231 | 2.1 |  |  | 15 |
| 5th coating | 737 | 32 | 234 | 9.3 | 69 | 300 | 2.7 |  |  | 16 |
| 6th coating | 1,001 | 33 | 328 | 9.6 | 96 | 396 | 3.5 | 16.4 | 2.8 | 6 |
|  |  |  |  |  |  |  |  |  |  | 414 |

Charge of T 375 clay beads (g)   11,250
Charge of Degussa silica (g)   414
Charge of RuCl$_3$.xH$_2$O (g)   957
Charge of SnO$_2$ (g)   1,361

TOTAL (g)   13,982
Total mass recovered after final drying =   14,080 g
Total dried mass of active-phase precursor   2,416 g CATALYST II: Preparation of a batch of 9 liters of 3.1% Ru/T375 ex-clay bead catalyst with an Sn/Ru ratio of 3

|  | Weight of active phase (g) | % of SnO$_2$ in the active phase | g of SnO$_2$ introduced | % Ru in the active phase | g of Ru introduced | Total Ru introduced (g) | % Ru/beads | % Ru relative to precursor | % Ru relative to recovered mass | g of Degussa 50 SiO$_2$ introduced |
|---|---|---|---|---|---|---|---|---|---|---|
| 1st coating | 545 | 30 | 162 | 6.6 | 36 | 36 | 0.3 |  |  | 7 |
| 2nd coating | 580 | 30 | 166 | 6.6 | 37 | 73 | 0.6 |  |  | 28 |
| 3rd coating | 620 | 30 | 184 | 6.5 | 41 | 114 | 1.0 |  |  | 65 |
| 4th coating | 650 | 37 | 241 | 8.2 | 53 | 167 | 1.4 |  |  | 13 |
| 5th coating | 830 | 36 | 301 | 8.1 | 67 | 234 | 2.0 |  |  | 10 |
| 6th coating | 575 | 33 | 190 | 7.3 | 42 | 276 | 2.4 |  |  | 8 |
| 7th coating | 745 | 33 | 244 | 7.3 | 54 | 330 | 2.8 |  |  |  |
| 8th coating | 575 | 33 | 190 | 7.3 | 42 | 372 | 3.1 | 13.2 | 2.6 | 18 |
|  |  |  |  |  |  |  |  |  |  | 149 |

Charge of T 375 clay beads (g)   11,750
Charge of Degussa silica (g)   149
Charge of RuCl$_3$.xH$_2$O (g)   899
Charge of SnO$_2$ (g)   1,677

TOTAL (g)   14,475
Total mass recovered after final drying (g)   14,715
Total dried mass of active-phase precursor   2,816

What is claimed is:

1. A composition of matter usable as a catalyst in a reaction mixture comprising:

a support comprising at least one oxide chosen from oxides which are inert or capable of being made inert relative to the reaction mixture; and a metallic phase at least partially covering said support, of which at least part comprises an intermetallic ruthenium-tin compound at least some of which is in the form of the defined compound Ru$_3$Sn$_7$, said metallic phase having a Sn/Ru atomic ratio of at least equal to ⅔ and at most equal to 3.

2. A composition according to claim 1, wherein said support is made inert by the action of gaseous hydrofluoric acid without losing its external geometry.

3. A composition according to claim 1, wherein said metallic phase contains at least 50%, of $Ru_3Sn_7$ compound.

4. A composition according to claim 3, wherein said metallic phase contains at least 90%, of $Ru_3Sn_7$ compound.

5. A composition according to claim 1, wherein the mass ratio between said support and said metallic phase is between 0.5% and 10%.

6. A composition according to claim 1, wherein the mass ratio between said support and said metallic phase is between 1% and 5%.

7. A composition according to claim 1, wherein said support is an oxide containing aluminum.

8. A composition according to claim 1, wherein said support has a silicon content which, expressed as $SiO_2$, is at most equal to ⅔ of the total weight of the composition of matter.

9. A composition according to claim 8, wherein said support has a silicon content which, expressed as $SiO_2$, is at most equal to ¼ of the total weight of the composition of matter.

10. A composition according to claim 1, wherein at least 90%, of the ruthenium present on said support is in the form of the said metallic phase covering said support.

11. A composition according to claim 10, wherein at least 98%, of the ruthenium present on said support is in the form of the said metallic phase covering said support.

12. A process for the treatment of carboxylic compounds to give aldehydes or derivatives thereof, comprising the steps of subjecting the carboxylic compound to hydrogenation in the presence of a catalyst comprising a composition of matter as defined in claim 1.

* * * * *